United States Patent [19]

Malamas et al.

[11] Patent Number: 5,420,146

[45] Date of Patent: May 30, 1995

[54] DI-OXADIAZOLIDINE DERIVATIVES AS ANTIHYPERGLYCEMIC AGENTS

[75] Inventors: Michael S. Malamas, Jamison, Pa.; Cynthia L. Palka, Bordentown; Iwan Gunawan, Somerset, both of N.J.

[73] Assignee: American Home Products Corporation, Madison, N.J.

[21] Appl. No.: 241,116

[22] Filed: May 10, 1994

[51] Int. Cl.[6] .................. C07D 9/62; A61K 31/535
[52] U.S. Cl. ........................ 514/364; 548/132
[58] Field of Search .................. 548/132; 514/364

[56] References Cited

U.S. PATENT DOCUMENTS

| | | | |
|---|---|---|---|
| 3,657,264 | 4/1972 | Rucker et al. | 548/132 |
| 3,994,909 | 11/1976 | Pommer et al. | 548/132 |
| 4,690,704 | 9/1987 | Aoki et al. | 548/132 |
| 5,334,604 | 8/1994 | Goldstein et al. | 548/132 |

FOREIGN PATENT DOCUMENTS

| | | | |
|---|---|---|---|
| 2612186 | 9/1988 | France | 548/132 |
| 58-0021670 | 2/1983 | Japan | 548/132 |
| 1189315 | 4/1970 | United Kingdom | 548/132 |
| 9203425 | 3/1992 | WIPO . | |

*Primary Examiner*—Johann Richter
*Assistant Examiner*—Catherine S. Kilby Scalzo
*Attorney, Agent, or Firm*—Robert F. Boswell, Jr.

[57] ABSTRACT

This invention relates to novel 2-[4-(5-substituted-1,2,4-oxadiazol-3-ylmethoxy)benzyl]-1,2,5-oxadiazolidine-3,5-diones which have demonstrated antihyperglycemic activity in diabetic (ob/ob and db/db) mice, genetic animal models of non-insulin dependent diabetes mellitus (NIDDM or Type II diabetes). These compounds are represented by Formula I below:

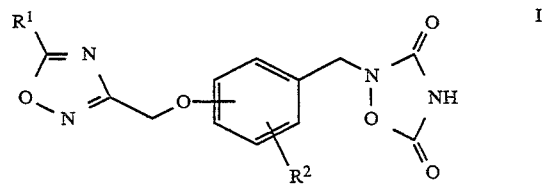

wherein $R^1$ is $C_6$–$C_{10}$ aryl, optionally substituted by one to three substituents independently selected from $C_1$–$C_6$ alkyl, $C_1$–$C_6$ alkoxy, fluorine, chlorine, bromine, iodine, $C_1$–$C_3$ trifluoroalkyl or $C_1$–$C_3$ trifluoroalkoxy; and $R^2$ is selected from the group consisting of hydrogen, $C_1$–$C_6$ alkyl, fluorine, chlorine, bromine, iodine, $C_1$–$C_6$ alkoxy, $C_1$–$C_3$ trifluoroalkyl, and $C_1$–$C_3$ trifluoroalkoxy, or a pharmaceutically acceptable salt thereof.

6 Claims, No Drawings

DI-OXADIAZOLIDINE DERIVATIVES AS ANTIHYPERGLYCEMIC AGENTS

FIELD OF INVENTION

This invention relates to novel 2-[4-(5-substituted-1,2,4-oxadiazol-3-ylmethoxy)benzyl]-1,2,5-oxadiazolidine-3,5-diones represented by Formula I below. These di-oxadiazole derivatives have demonstrated antihyperglycemic activity in diabetic (ob/ob and db/db) mice, genetic animal models of non-insulin dependent diabetes mellitus (NIDDM or Type II diabetes). The Formula I compounds or pharmaceutical compositions thereof are therefore useful in treating hyperglycemic in mammals having non-insulin dependent diabetes mellitus.

BACKGROUND OF THE INVENTION

Diabetes mellitus is a syndrome characterized by abnormal insulin production, increased urinary output and elevated blood glucose levels. There are two major subclasses of diabetes mellitus. One is the insulin-dependent diabetes mellitus (IDDM or Type I), formerly referred to as juvenile onset diabetes since it was evident early in life, and noninsulin dependent diabetes mellitus (NIDDM or Type II), often referred to as maturity-onset diabetes. Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs requiring much higher doses of insulin than normal. Another shortcoming of insulin is that while it may control hormonal abnormalities, it does not always prevent the occurrence of complications such as neuropathy, retinopathy, glomerulosclerosis, or cardiovascular disorders.

Orally effective antihyperglycemic agents are used to reduce blood glucose levels and to reduce damage to the nervous, retinal, renal or vascular systems through mechanisms affecting glucose metabolism. Such agents act in a variety of different mechanisms including inhibition of fatty acid oxidation, α-glycosidase inhibition, antagonism of $\alpha_2$-receptors and inhibition of gluconeogenesis. Two classes of compounds have predominated: the biguanides as represented by phenformin and the sulfonylureas as represented by tolbutamide (Orinase®). A third class of compounds which has shown antihyperglycemic activity are thiazolidinediones of which ciglitazone is the prototype. Ciglitazone suppresses the symptoms of diabetes-hyperglycemia, hypertriglyceridemia and hyperinsulinemia [Diabetes 32, 804–10 (1983)].

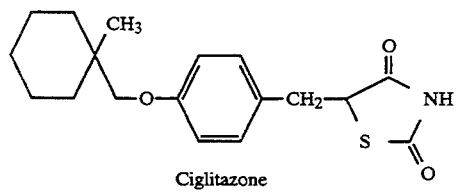

Ciglitazone

Still another class of antihyperglycemic agents are the N-arylalkyl-N-hydroxy ureas and the 2-(arylalkyl)-[1,2,4]-oxadiazolidine-3,5-diones. The published PCT patent application WO 92/03425 discloses compounds of the formula:

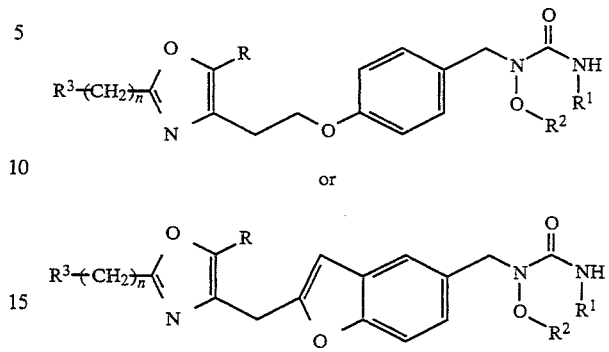

where $R^1$ and $R^2$ are independently H, $C_1$–$C_9$ alkyl, $C_3$–$C_7$ cycloalkyl, phenyl, etc. or $R^1$ and $R^2$ together are carbonyl, which have utility as hypoglycemic or hypocholesteremic agents.

The hypoglycemic properties of these compounds in ob/ob mice are discussed by Goldstein et al. J. Med. Chem. 36, 2238-2240 (1993).

SUMMARY OF THE INVENTION

The compounds of this invention are represented by Formula I:

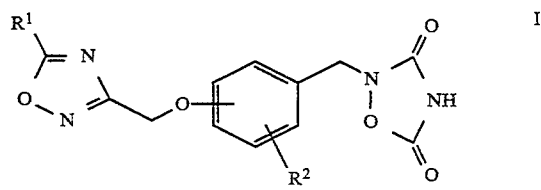

wherein $R^1$ is $C_6$–$C_{10}$ aryl, optionally substituted by one to three substituents independently selected from $C_1$–$C_6$ alkyl, $C_1$–$C_6$ alkoxy, fluorine, chlorine, bromine, iodine, $C_1$–$C_3$ trifluoroalkyl or $C_1$–$C_3$ trifluoroalkoxy; and $R^2$ is selected from the group consisting of hydrogen, $C_1$–$C_6$ alkyl, fluorine, chlorine, bromine, iodine, $C_1$–$C_6$ alkoxy, $C_1$–$C_3$ trifluoroalkyl, and $C_1$–$C_3$ trifluoroalkoxy, or a pharmaceutically acceptable salt thereof.

In the above definition of the variables $R^1$ and $R^2$, $C_6$–$C_{10}$ aryl is phenyl, 1-naphthyl or 2-naphthyl; $C_1$–$C_6$ alkyl includes straight and branched chain alkyl groups having from one to six carbon atoms, $C_1$–$C_6$ alkoxy is an O—$C_1$–$C_6$ alkyl group where the $C_1$–$C_6$ alkyl group is as previously defined, $C_1$–$C_3$ trifluoroalkyl is trifluoromethyl, 2,2,2-trifluoroethyl, or 3,3,3-trifluoropropyl; and $C_1$–$C_3$ trifluoroalkoxy is an O—$C_1$–$C_3$ trifluoroalkyl group where the $C_1$–$C_3$ trifluoroalkyl moiety is as defined above.

The antihyperglycemic activities of the invention compounds were determined in vivo in the diabetic ob/ob or db/db mouse, genetic animal models of non-insulin-dependent diabetes mellitus (NIDDM). Compounds of this invention lower blood glucose and insulin in the ob/ob mouse and lower blood glucose in the db/db mouse and thus provide a method for the treatment of non-insulin-dependent diabetes mellitus. This invention further provides for a pharmaceutical composition for the treatment of NIDDM. Pharmaceutically acceptable salts may be formed between an invention compound and an alkali metal or alkaline earth metal such as sodium, potassium, calcium or barium. It should also be recognized that an invention compound or salt thereof may be isolated and purified as a solvate or hydrate and are considered to be the equivalent of the invention compound or salt thereof.

DETAILED DESCRIPTION OF THE INVENTION

The compounds of the present invention may be prepared according to the following synthetic schemes using standard laboratory procedures. The starting materials used in these synthetic schemes are either commercially available or can be prepared by known methods conventional in the art (Heterocyclic Compounds Vol 34, 1979 and Heterocyclic Compounds Vol. 45, 1985).

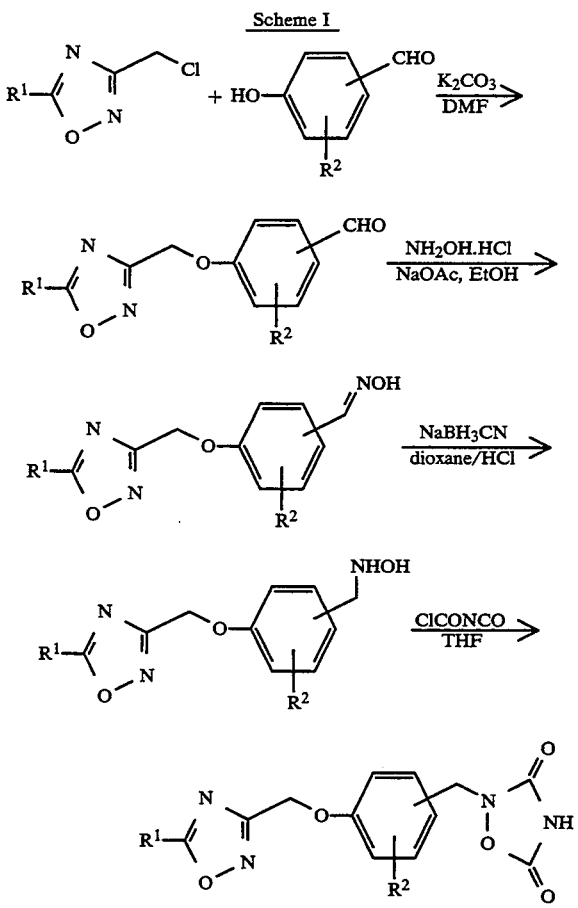

where $R^1$ and $R^2$ are as defined above.

The intermediate 3-chloromethyl-5-substituted-1,2,4-oxadiazole used in Scheme I may be prepared according to Scheme II. Example 11 is a specific example of this synthesis.

Scheme II

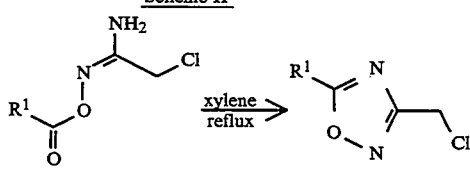

where $R^1$ is as defined above.

The following specific examples are included to illustrate the above synthetic methods and are not intended to limit this disclosure in any way. Still other methods of preparation of the invention compounds may be apparent to those skilled in the art of organic synthesis.

EXAMPLE 1

2-{3-[5-(4-Trifluoromethoxy-phenyl)-[1,2,4]oxadiazol-3-ylmethoxy]-benzyl}-[1,2,4]oxadiazolidine-3,5-dione Step a) 3-[5-(4-Trifluoromethoxy-phenyl)-[1,2,4]-oxadiazol-3-ylmethoxy]-benzaldehyde A mixture of 4-chloromethyl-2-(4-trifluoromethoxy-phenyl)-oxadiazole (8.89 g, 36.6 mmol), 3-hydroxybenzaldehyde (4.92 g, 40.2 mmol), potassium carbonate (7.58 g, 54.9 mmol) and dimethylformamide (150 mL) was stirred at 70° C. for 3 hours. The mixture was then poured into $H_2O$, acidified with HCl (1N), and extracted with EtOAc. The organic extracts were washed twice with NaOH (2.5N), then washed with brine, dried over $MgSO_4$, and charcoalized for 15 minutes. Filtration through SOLKA FLOC®, followed by evaporation and crystallization from EtOAc/hexane, gave a white solid (6.9 g, 52% yield, m.p. 79°-80° C.).

Analysis for: $C_{17}H_{11}F_3N_2O_4$ Calc'd: C, 56.05; H, 3.04; N, 7.69 Found: C, 55.86; H, 3.04; N, 8.06

Step b) 3-[5-(4-Trifluoromethoxy-phenyl)-[1,2,4]-oxadiazol-3-ylmethoxy]-benzaldehyde oxime To a solution of 3-[5-(4-trifluoromethoxy-phenyl)-[1,2,4]-oxadiazol-3-ylmethoxy]-benzaldehyde (4.0 g, 11.0 mmol), in ethanol (150 mL), were added hydroxylamine hydrochloride (2.29 g, 33.0 mmol) and a solution of sodium acetate (3.60 g, 44.0 mmol) in $H_2O$ (30 mL). The mixture was stirred at 50° C. for 2 hours. The EtOH was evaporated in vacuo, then the residue was taken into $H_2O$. The precipitated product was filtered, washed with hexane, and dried via suction filtration. Recrystallization from EtOAc/hexane gave a white solid (4.03 g, 96% yield, m.p. 130°-131° C.)

Analysis for: $C_{17}H_{12}F_3N_3O_4$ Calc'd: C, 53.83; H,3.19; N, 11.08 Found: C, 53.60; H, 3.13; N, 10.98

Step c) 2-{3-[5-(4-Trifluoromethoxy-phenyl)-[1,2,4]-oxadiazol-3-ylmethoxy]-benzyl}-hydroxylamine To a solution of 3-[5-(4-Trifluoromethoxy-phenyl)-[1,2,4]-oxadiazol-3-ylmethoxy]-benzaldehyde oxime (3.99 g, 10.5 mmol) in MeOH (200 mL) and THF (40 mL) was added sodium cyanoborohydride (3.28 g, 52.6 mmol). A solution of 4N HCl in dioxane was then added dropwise in order to maintain a pH range 3 to 4. Upon completion verified by TLC, the reaction mixture was poured into $H_2O$, basified with 2N NaOH to a pH of about 8 to 9 and extracted with EtOAc. The organic extracts were dried over $MgSO_4$. Evaporation and crystallization from EtOAc/hexane gave a white solid (3.15 g, 78% yield, m.p. 110°-111° C.).

Analysis for: $C_{17}H_{14}F_3N_3O_4$ Calc'd: C, 53.55; H, 3.70; N, 11.02 Found: C, 53.54; H, 3.70; N, 10.91

Step d) 2-{3-[5-(4-Trifluoromethoxy-phenyl)-[1,2,4]oxadiazol-3-ylmethoxy]-benzyl}-[1,2,4]oxadiazolidine-3,5-dione To a cold ($-5°$ C.) solution of 2-{3-[5-(4-trifluoromethoxy-phenyl)-[1,2,4]-oxadiazol-3-ylmethoxy]-benzyl}-hydroxylamine (3.12 g, 8.16 mmol) in anhydrous THF (30 ml) was added N-(chlorocarbonyl)isocyanate (0.66 ml, 8.16 mmol) dropwise. The mixture was stirred for 30 minutes, poured into HCl (2N) and extracted with EtOAc. Evaporation and purification by flash chromatography on acid washed (5% $H_3PO_4$/MeOH) silica gel (eluting solvent EtOAc/hexane ⅓), gave a white solid (2.24 g, 60% yield, m.p. 120°–121° C.

Analysis for: $C_{19}H_{13}F_3N_4O_6$ Calc'd: C, 50.68; H, 2.91; N, 12.44 Found: C, 50.68; H, 2.86; N, 12.32

EXAMPLE 2

2-{4-[5-(4-Trifluoromethoxy-phenyl)-[1,2,4]oxadiazol-3-ylmethoxy]-benzyl}-[1,2,4]oxadiazolidine-3,5-dione The title compound was prepared in substantially the same manner as described in example 1. 4-Hydroxybenzaldehyde was used in place of 3-hydroxybenzaldehyde. The title compound was obtained as a white solid, m.p. 147°–148° C.

Analysis for: $C_{19}H_{13}F_3N_4O_6$ Calc'd: C, 50.68; H, 2.91; N, 12.44 Found: C, 50.79; H, 2.90; N, 12.40

EXAMPLE 3

2-{3-[5-(4-Chloro-phenyl)-[1,2,4]oxadiazol-3-ylmethoxy]-benzyl}-[1,2,4]oxadiazolidine-3,5-dione The title compound was prepared in substantially the same manner as described in example 1, and was obtained as a white solid, m.p. 159°–160° C.

Analysis for: $C_{18}H_{13}ClN_4O_5$ Calc'd: C, 53.94; H, 3.27; N, 13.98 Found: C, 54.31; H, 3.29; N, 14.22

EXAMPLE 4

2-{4-[5-(4-Chloro-phenyl)-[1,2,4]oxadiazol-3-ylmethoxy]-benzyl}-[1,2,4]oxadiazolidine-3,5-dione The title compound was prepared in substantially the same manner as described in example 1. 4-Hydroxybenzaldehyde was used in place of 3-hydroxybenzaldehyde. The title compound was obtained as a white solid, m.p. 168°–169° C.

Analysis for: $C_{18}H_{13}ClN_4O_5$ Calc'd: C, 53.94; H, 3.27; N, 13.98 Found: C, 54.04; H, 3.19; N, 13.91

EXAMPLE 5

2-[4-(5-Phenyl-[1,2,4]oxadiazol-3-ylmethoxy)-benzyl]-[1,2,4]oxadiazolidine-3,5-dione The title compound was prepared in substantially the same manner as described in example 1, and was obtained as a white solid, m.p. 150°–151° C.

Analysis for: $C_{18}H_{14}N_4O_5$ Calc'd: C, 59.02; H, 3.85; N, 15.29 Found: C, 59.07; H, 3.56; N, 15.17

EXAMPLE 6

2-[3-(5-Phenyl-[1,2,4]oxadiazol-3-ylmethoxy)-benzyl]-[1,2,4]oxadiazolidine-3,5-dione The title compound was prepared in substantially the same manner as described in example 1, and was obtained as a white solid, m.p. 133°–134° C.

Analysis for: $C_{18}H_{14}N_4O_5$ Calc'd: C, 59.02; H, 3.85; N, 15.29 Found: C, 58.87; H, 3.73; N, 15.41

EXAMPLE 7

2-{3-[5-(4-Trifluoromethyl-phenyl)-[1,2,4]oxadiazol-3-ylmethoxy]-benzyl}-[1,2,4]oxadiazolidine-3,5-dione The title compound was prepared in substantially the same manner as described in example 1, and was obtained as a white solid, m.p. 90°–91° C.

Analysis for: $C_{19}H_{13}F_3N_4O_5$ Calc'd: C, 52.54; H, 3.02; N, 12.90 Found: C, 52.36; H, 2.89; N, 12.83

EXAMPLE 8

2-{4-[5-(4-Trifluoromethyl-phenyl)-[1,2,4]oxadiazol-3-ylmethoxy]-benzyl}-[1,2,4]oxadiazolidine-3,5-dione The title compound was prepared in substantially the same manner as described in example 1. 4-Hydroxybenzaldehyde was used in place of 3-hydroxybenzaldehyde. The title compound was obtained as a white solid, m.p. 160°–161° C.

Analysis for: $C_{19}H_{13}F_3N_4O_5$ Calc'd: C, 52.55; H, 3.02; N, 12.90 Found: C, 52.46; H, 2.74; N, 12.94

EXAMPLE 9

2-{3-[5-(4-Fluoro-phenyl)-[1,2,4]oxadiazol-3-ylmethoxy]-benzyl}-[1,2,4]oxadiazolidine-3,5-dione The title compound was prepared in substantially the same manner as described in example 1, and was obtained as a white solid, m.p. 147°–148° C.

Analysis for: $C_{18}H_{13}FN_4O_5$ Calc'd: C, 56.25; H, 3.41; N, 14.58 Found: C, 56.33; H, 3.51; N, 14.87

EXAMPLE 10

2-{4-[5-(4-Fluoro-phenyl)-[1,2,4]oxadiazol-3-ylmethoxy]-benzyl}-[1,2,4]oxadiazolidine-3,5-dione The title compound was prepared in substantially the same manner as described in example 1. 4-Hydroxybenzaldehyde was used in place of 3-hydroxybenzaldehyde. The title compound was obtained as a white solid, m.p. 156°–157° C.

Analysis for: $C_{18}H_{13}FN_4O_5$ Calc'd: C, 56.25; H, 3.41; N, 14.58 Found: C, 56.46; H, 3.45; N, 14.48

EXAMPLE 11

This example shows the preparation of compounds presented in Scheme II.

Step a) 2-chloro-N-(4-fluorobenzoyloxy)-acetimidamide

To a mixture of 2-chloro-N-hydroxy-acetimidamide (15.5 g, 143.3 mmol) prepared according to Flora et al., *Cancer Research* 38, 1291–1295 (1978), potassium carbonate (19.78 g, 143.3 mmol), and dioxane (200 ml), was added 4-fluorobenzoyl chloride (25 g, 157.7 mmol) in dioxane (60 ml), dropwise over a 15 min period. The mixture was stirred at room temperature for 4 hours, them poured into water, and basified with saturated $NaHCO_3$ solution. The precipitated product was collected by suction filtration and dried to yield an off-white solid (31.87 g, 96% yield, m.p. 115°–116° C.).

Analysis for: $C_9H_8FClN_2O_2$ Calc'd: C, 46.87; H, 3.50; N, 12.15 Found: C, 46.57; H, 3.32; N, 12.51

Step b) 4-chloromethyl-2-(4-fluorophenyl)-[1,2,4]oxadiazole

A suspension of 2chloro-N-(4-fluorobenzoyloxy)-acetimidamide (31.85 g, 138.2 mmol) in xylene was heated to 160° C. and refluxed for 16 hours. The solvent was removed in vacuo, and the dark brown oil purified by flash chromatography on silica gel (eluting solvent EtOAc/hexane 1/20), to give an off-white solid (13.92 g, 47% yield, m.p. 47°–48° C.).

Analysis for: $C_9H_6FClN_2O$ Calc'd: C, 50.84; H, 2.84; N, 13.18 Found: C, 50.99; H, 2.89; N, 13.17

PHARMACOLOGY

The diabetic db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia (1). Furthermore, the db/db mouse will eventually develop some of the long-term complications that have been associated with diabetes mellitus (1). In spite of these commonalities, the acute administration of sulfonylureas (even at extremely high doses) will not reduce the hyperglycemia of the db/db mouse (2). The ability of a few other hypoglycemic agents to be effective in this species suggest that the other agents have mechanism of action which are different from that of the sulfonylureas (2,3,4,5). Such compounds, therefore, are more likely to be efficacious in the population of type II diabetic patients that do not respond to sulfonylurea therapy.

Determination of Blood Glucose Lowering in db/db Mice.

On the morning of Day 1, 35 mice [male diabetic db/db (C57BL/KsJ) mice (Jackson Laboratories), 2–7 months of age and 50–70 g] were fasted for 4 hours, weighed and a baseline blood sample (15–30 µl) was collected from the tail-tip of each mouse without anesthesia, and placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels (N=6 for vehicle and N=4 for each drug group). On the afternoon of Days 1, 2 and 3, the vehicle, control or test drugs were administered (p.o.) to the ad libitum fed mice. On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hrs after drug administration. The plasma was separated and levels of glucose in plasma was determined by the Abbott VP Analyzer.

For each mouse, the percent change of its plasma glucose level on Day 4 (mean of the 2 and 4 hr samples) from respective level before drug administration (Day 1 baseline sample) is determined as follows:

$$\frac{\text{mean of 2 and 4 hr samples (Day 4)}}{\text{Baseline Sample (Day 1)}} \times 100$$

Analysis of variance followed by Dunnett's multiple comparison (one-sided) will be used to estimate the degree of statistical significance of the difference between the vehicle control group and the individual drug-treated groups. A drug will be considered active, at the specific dosage administered, if the difference of the plasma glucose level has a $p<0.05$. The actual difference between the mean percent change of the vehicle and drug-treated groups is shown in Table 1.

The positive control, ciglitazone produces a 18 to 34% decrease in plasma glucose levels at 100 mg/kg/day×4 days, p.o.

TABLE 1

| Compound of Example No. | Dose mg/kg, p.o. | % Change glucose |
|---|---|---|
| 1 | 100 | −48 |
| 2 | 100 | −25 |
| 8 | 100 | −40 |

References:
1. Coleman, D. L. (1982) Diabetes-obesity syndromes in mice. Diabetes 31 (Suppl. 1); 1–6.
2. Tutwiler, G. F., T. Kirsch, and G. Bridi (1978). A pharmacologic profile of McN-3495 [N-(1-methyl-2-pyrrolidinylidene)-N'-phenyl-1-pyrrolidine-carboximidamide], a new, orally effective hypoglycemic agent. Diabetes 27:856–857.
3. Lee, S. M., G. Tutwiler, R. Bressler, and C. H. Kircher (1982). Metabolic control and prevention of nephropathy by 2-tetradecylglycidate in the diabetic mouse (db/db). Diabetes 31:12–18.
4. Chang, A. Y., B. W. Wyse, B. J. Gilchrist, T. Peterson, and R. Diani (1983) Ciglitazone, a new hypoglycemic agent. 1. Studies in ob/ob and db/db mice, diabetic Chinese hamsters, and normal and streptozocin-diabetic rats. Diabetes 32: 830–838.
5. Hosokawa, T., K. Ando, and G. Tamura (1985). An ascochlorin derivative, AS-6, reduces insulin resistance in the genetically obese diabetic mouse, db/db. Diabetes 34: 267–274.

Determination of Blood Glucose Lowering Effect in ob/ob mice

The non-insulin-dependent diabetic syndrome can be typically characterized by obesity, hyperglycemia, abnormal insulin secretion, hyperinsulinemia and insulin resistance. The genetically obese-hyperglycemic ob/ob mouse exhibits many of these metabolic abnormalities and is thought to be a useful media to search for hypoglycemic agents to treat NIDDM (Coleman, 1978)

Male or female ob/ob mice (C57B1/6J), ages 2 to 5 months (10 to 65 g), of a similar age are randomized according to plasma glucose into 4 groups of 10 mice. The mice are housed 5 per cage and are maintained on normal rodent chow with water ad libitum. The mice receive test compound daily. The test compound is suspended in 0.5 mL of 0.5% methyl cellulose and is administered by gavage (dissolved in drinking water) or admixed in the diet. The dose of compound given ranges from 2.5 to 200 mg/kg/day. Body weight of fed animals is measured at the beginning of each week and doses for the entire week are calculated using this weight and are expressed in terms of the active moiety of the compound. Control mice receive vehicle only.

On the morning of Days 4, 7 or 14 two drops of blood (approximately 50 µl) are collected into sodium fluoride containing tubes either from the tail vein or after decapitation. For those studies in which the compound is administered daily by gavage, the blood samples are collected four hour after compound administration. The plasma is isolated by centrifugation and the concentration of glucose is measured enzymatically on an Abbott V. P. Analyzer and the plasma concentration of insulin is determined by radioimmunoassay (Heding, 1972). For each mouse, the percentage change in plasma glucose on Day 4, 7 or 14 is calculated relative to the mean plasma glucose of the vehicle treated mice. Analysis of variance followed by Dunnett's Comparison Test (one tailed) is used to estimate the significant difference between the plasma glucose values from the control group and the individual compound treated groups. The results are presented in Table II.

TABLE II

| Compound of Example No. | Dose mg/kg, p.o. | % Change glucose | % Change insulin |
|---|---|---|---|
| 5 | 100 | −47 | −87 |
| 6 | 75 | −34 | −53 |
| 7 | 75 | −46 | −45 |
| 8 | 100 | −20 | −73 |
| 10 | 100 | −31 | −88 |

References:
1. Brichard, S., Bailey, C. and Henquin, J.: Marked improvement of glucose homeostasis in diabetic ob/ob mice given oral vanadate. Diabetes 39: 1326–1332, 1990.
2. Chang, A., Wyse, B., Gilchrist, B., Peterson, T. and Diani, A.: Ciglitazone, a new hypoglycemic agent. I. Studies in ob/ob and db/db mice, diabetic Chinese hamsters, and normal and streptozoticin-induced diabetic rats. Diabetes 32: 830–838, 1983.
3. Coleman, D.: Obese and diabetes: Two mutant genes causing diabetes-obesity syndromes in mice. Diabetologia 14: 141–148, 1978.
4. Heding, L. G.: Determination of total serum insulin (IRI) in insulin-treated diabetic patients. Diabetologia 8: 260–266, 1972.

PHARMACEUTICAL COMPOSITION

Based on the results of the pharmacological assay, the compounds of this invention are useful in the treatment of hyperglycemia in diabetes mellitus.

The compounds may be administered neat or with a pharmaceutical carrier to a mammal in need thereof. The pharmaceutical carrier may be solid or liquid and the active compound shall be a therapeutically effective amount.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. A dosage range of from 0.1 to 200 mg/kg/day is contemplated, with a preferred dosage of from 0.1 to 100 mg/kg/day. Due to uncertainty in relating laboratory mouse study data to other mammals, the degree of hyperglycemia, and the compound selected, the dosages used in the treatment of non-insulin dependent diabetes mellitus must be subjectively determined by a physician or veterinarian according to standard medical or veterinary practice.

What is claimed is:
1. A compound having the formula:

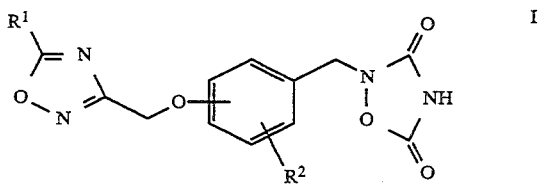

wherein
R$^1$ is phenyl or naphthyl, optionally substituted by one to three substituents independently selected from C$_1$–C$_6$ alkyl, C$_1$–C$_6$ alkoxy, fluorine, chlorine, bromine, iodine, C$_1$–C$_3$ trifluoroalkyl or C$_1$–C$_3$ trifluoroalkoxy; and R$^2$ is selected from the group consisting of hydrogen, C$_1$–C$_6$ alkyl, fluorine, chlorine, bromine, iodine, C$_1$–C$_6$ alkoxy, C$_1$–C$_3$ trifluoroalkyl, and C$_1$–C$_3$ trifluoroalkoxy, or a pharmaceutically acceptable salt thereof.

2. A compound according to claim 1 selected from the group consisting of:
2-{3-[5-(4-trifluoromethoxy-phenyl)-[1,2,4]oxadiazol-3-ylmethoxy]-benzyl}-[1,2,4]oxadiazolidine-3,5-dione, 2-{4-[5-(4-trifluoromethoxy-phenyl)-[1,2,4]oxadiazol-3-ylmethoxy]-benzyl}-[1,2,4]oxadiazolidine-3,5-dione, 2-{3-[5-(4-chloro-phenyl)-[1,2,4]oxadiazol-3-ylmethoxy]-benzyl}-[1,2,4]oxadiazolidine-3,5-dione, 2-{4-[5-(4-chloro-phenyl)-[1,2,4]oxadiazol-3-ylmethoxy]-benzyl}-[1,2,4]oxadiazolidine-3,5-dione, 2-[4-(5-phenyl-[1,2,4]oxadiazol-3-ylmethoxy)-benzyl]-[1,2,4]oxadiazolidine-3,5-dione, 2-[3-(5-phenyl-[1,2,4]oxadiazol-3-ylmethoxy)-benzyl]-[1,2,4]oxadiazolidine-3,5-dione, 2-{3-[5-(4-trifluoromethyl-phenyl)-[1,2,4]oxadiazol-3-ylmethoxy]-benzyl}-[1,2,4]oxadiazolidine-3,5-dione, 2-{4-[5-(4-trifluoromethyl-phenyl)-[1,2,4]oxadiazol-3-ylmethoxy]-benzyl}-[1,2,4]oxadiazolidine-3,5-dione, 2-{3-[5-(4-fluoro-phenyl)-[1,2,4]oxadiazol-3-ylmethoxy]-benzyl}-[1,2,4]oxadiazolidine-3,5-dione, and 2-{4-[5-(4-fluoro-phenyl)-[1,2,4]oxadiazol-3-ylmethoxy]-benzyl}-[1,2,4]oxadiazolidine-3,5-dione, or a pharmaceutically acceptable salt thereof.

3. A method of treating hyperglycemia in a mammal which comprises administering to a mammal having hyperglycemia a therapeutically effective amount of a compound having the formula:

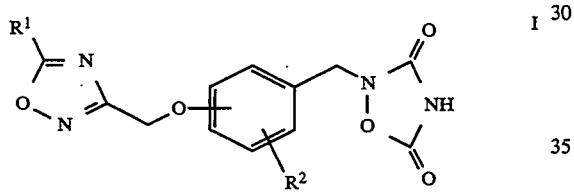

wherein $R^1$ is phenyl or naphthyl, optionally substituted by one to three substituents independently selected from $C_1$–$C_6$ alkyl, $C_1$–$C_6$ alkoxy, fluorine, chlorine, bromine, iodine, $C_1$–$C_3$ trifluoroalkyl or $C_1$–$C_3$ trifluoroalkoxy; and $R^2$ is selected from the group consisting of hydrogen, $C_1$–$C_6$ alkyl, fluorine, chlorine, bromine, iodine, $C_1$–$C_6$ alkoxy, $C_1$–$C_3$ trifluoroalkyl, and $C_1$–$C_3$ trifluoroalkoxy, or a pharmaceutically acceptable salt thereof.

4. A method of treating hyperglycemia according to claim 3 wherein the compound used is selected from the group consisting of:

2-{3-[5-(4-trifluoromethoxy-phenyl)-[1,2,4]oxadiazol-3-ylmethoxy]-benzyl}-[1,2,4]oxadiazolidine-3,5-dione, 2-{4-[5-(4-trifluoromethoxy-phenyl)-[1,2,4]oxadiazol-3-ylmethoxy]-benzyl}-[1,2,4]oxadiazolidine-3,5-dione, 2-{3-[5-(4-chloro-phenyl)-[1,2,4]oxadiazol-3-ylmethoxy]-benzyl}-[1,2,4]oxadiazolidine-3,5-dione, 2-{4-[5-(4-chloro-phenyl)-[1,2,4]oxadiazol-3-ylmethoxy]-benzyl}-[1,2,4]oxadiazolidine-3,5-dione, 2-[4-(5-phenyl-[1,2,4]oxadiazol-3-ylmethoxy)-benzyl]-[1,2,4]oxadiazolidine-3,5-dione, 2-[3-(5-phenyl-[1,2,4]oxadiazol-3-ylmethoxy)-benzyl]-[1,2,4]oxadiazolidine-3,5-dione, 2-{3-[5-(4-trifluoromethyl-phenyl)-[1,2,4]oxadiazol-3-ylmethoxy]-benzyl}-[1,2,4]oxadiazolidine-3,5-dione, 2-{4-[5-(4-trifluoromethyl-phenyl)-[1,2,4]oxadiazol-3-ylmethoxy]-benzyl}-[1,2,4]oxadiazolidine-3,5-dione, 2-{3-[5-(4-fluoro-phenyl)-[1,2,4]oxadiazol-3-ylmethoxy]-benzyl}-[1,2,4]oxadiazolidine-3,5-dione, and 2-{4-[5-(4-fluoro-phenyl)-[1,2,4]oxadiazol-3-ylmethoxy]-benzyl}-[1,2,4]oxadiazolidine-3,5-dione, or a pharmaceutically acceptable salt thereof.

5. A pharmaceutical composition for the treatment of hyperglycemia in mammals which comprises a pharmaceutically acceptable carrier and a therapeutically effective amount of a compound having the formula:

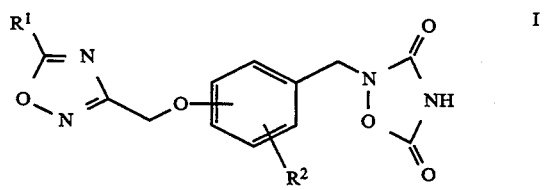

wherein $R^1$ is phenyl or naphthyl, optionally substituted by one to three substituents independently selected from $C_1$–$C_6$ alkyl, $C_1$–$C_6$ alkoxy, fluorine, chlorine, bromine, iodine, $C_1$–$C_3$ trifluoroalkyl or $C_1$–$C_3$ trifluoroalkoxy; and $R^2$ is selected from the group consisting of hydrogen, $C_1$–$C_6$ alkyl, fluorine, chlorine, bromine, iodine, $C_1$–$C_6$ alkoxy, $C_1$–$C_3$ trifluoroalkyl, and $C_1$–$C_3$ trifluoroalkoxy, or a pharmaceutically acceptable salt thereof.

6. A pharmaceutical composition according to claim 5 wherein the compound used is selected from the group consisting of:

2-{3-[5-(4-trifluoromethoxy-phenyl)-[1,2,4]oxadiazol-3-ylmethoxy]-benzyl}-[1,2,4]oxadiazolidine-3,5-dione, 2-{4-[5-(4-trifluoromethoxy-phenyl)-[1,2,4]oxadiazol-3-ylmethoxy]-benzyl}-[1,2,4]oxadiazolidine-3,5-dione, 2-{3-[5-(4-chloro-phenyl)-[1,2,4]oxadiazol-3-ylmethoxy]-benzyl}-[1,2,4]oxadiazolidine-3,5-dione, 2-{4-[5-(4-chloro-phenyl)-[1,2,4]oxadiazol-3-ylmethoxy]-benzyl}-[1,2,4]oxadiazolidine-3,5-dione, 2-[4-(5-phenyl-[1,2,4]oxadiazol-3-ylmethoxy)-benzyl]-[1,2,4]oxadiazolidine-3,5-dione, 2-[3-(5-phenyl-[1,2,4]oxadiazol-3-ylmethoxy)-benzyl]-[1,2,4]oxadiazolidine-3,5-dione, 2-{3-[5-(4-trifluoromethyl-phenyl)-[1,2,4]oxadiazol-3-ylmethoxy]-benzyl}-[1,2,4]oxadiazolidine-3,5-dione, 2-{4-[5-(4-trifluoromethyl-phenyl)-[1,2,4]oxadiazol-3-ylmethoxy]-benzyl}-[1,2,4]oxadiazolidine-3,5-dione, 2-{3-[5-(4-fluoro-phenyl)-[1,2,4]oxadiazol-3-ylmethoxy]-benzyl}-[1,2,4]oxadiazolidine-3,5-dione, and 2-{4-[5-(4-fluoro-phenyl)-[1,2,4]oxadiazol-3-ylmethoxy]-benzyl}-[1,2,4]oxadiazolidine-3,5-dione, or a pharmaceutically acceptable salt thereof.

* * * * *